United States Patent [19]

Current

[11] Patent Number: 4,625,049
[45] Date of Patent: Nov. 25, 1986

[54] ALCOHOL CARBONYLATION PROCESS USING A BIMETALLIC NICKEL CATALYST

[75] Inventor: Steven P. Current, Novato, Calif.

[73] Assignee: Chevron Research Company, San Francisco, Calif.

[21] Appl. No.: 393,931

[22] Filed: Jun. 30, 1982

[51] Int. Cl.$^4$ .................... C07C 29/32; C07C 31/08; C07C 45/49; C07C 51/12; C07C 67/36; C07C 33/22

[52] U.S. Cl. .................... 560/232; 260/410.9 R; 260/413; 549/295; 560/97; 560/105; 560/114; 560/204; 560/206; 560/265; 562/406; 562/497; 562/519; 568/485; 568/486; 568/487; 568/715; 568/814; 568/852; 568/861; 568/902

[58] Field of Search ............... 560/114, 232, 265, 204, 560/105, 97, 206; 562/519, 406, 497; 568/902, 903, 715, 852, 814, 861, 594, 486, 485, 487; 260/410.9 R, 413

[56] References Cited

U.S. PATENT DOCUMENTS

| | | | |
|---|---|---|---|
| 2,593,440 | 4/1952 | Hagemeyer | 560/232 |
| 3,285,948 | 11/1966 | Butter | 568/902 |
| 3,387,043 | 6/1968 | Kuraishi et al. | 568/902 |
| 4,304,946 | 12/1981 | Isogai et al. | 568/902 |
| 4,431,835 | 2/1984 | Gauthier-Lafaye et al. | 560/105 |

FOREIGN PATENT DOCUMENTS 2089803A 6/1982 United Kingdom ............... 562/519

Primary Examiner—Vivian Garner
Attorney, Agent, or Firm—T. G. DeJonghe; C. J. Caroli

[57] ABSTRACT

A process for the preparation of carboxylic acids, alcohols, aldehydes or the secondary products thereof which comprises reacting an alcohol having from one to about twenty carbon atoms with hydrogen and carbon monoxide in the presence of a heterogeneous sulfided catalyst comprising nickel in admixture with a co-catalyst selected from the elements of Groups V-B, VI-B and the Actinide series of the Periodic Table.

10 Claims, No Drawings

ALCOHOL CARBONYLATION PROCESS USING A BIMETALLIC NICKEL CATALYST

BACKGROUND OF THE INVENTION

The present invention is concerned with a process for the preparation of oxygen-containing carbon compounds from alcohols and synthesis gas, wherein the compounds produced have at least one more carbon atom than the starting alcohol. More specifically, the present invention involves a process for the preparation of carboxylic acids, alcohols, aldehydes or the secondary products thereof by reaction of an alcohol with hydrogen and carbon monoxide in the presence of a heterogeneous bimetallic sulfided catalyst.

U.S. Pat. No. 2,623,906 discloses that at pressures above 1,000 atmospheres and in the presence of a cobalt catalyst, primary, secondary and tertiary alcohols react with synthesis gas to form glycol ethers and monohydric alcohols containing at least one more carbon atom per molecule than the original alcohol reactant.

U.S. Pat. No. 3,285,948 discloses that an improved yield of ethanol from methanol can be obtained by conducting the synthesis gas homologation reaction in the presence of a cobalt catalyst which is promoted with iodine and a metal halide selected from ruthenium halide and osmium halide.

U.S. Pat. No. 4,111,837 discloses a process for producing ethanol which comprises reacting methanol with carbon monoxide and hydrogen in the presence of a catalyst consisting essentially of a methanol-soluble cobalt carbonyl and methanol-insoluble rhenium metal.

U.S. Pat. No. 4,304,946 discloses a process for producing ethanol from methanol, carbon monoxide and hydrogen which comprises conducting the reaction in the presence of a cobalt sulfide or a mixture of a cobalt sulfide and at least one of a nitrogen-containing compound and a phosphorus compound.

SUMMARY OF THE INVENTION

The present invention relates to a process for the preparation of carboxylic acids, alcohols, aldehydes or the secondary products thereof which comprises reacting an alcohol with hydrogen and carbon monoxide at a temperature in the range of about 150° C. to 350° C. and a pressure in the range of about 500 psig to 5,000 psig in the presence of a heterogeneous sulfided catalyst comprising nickel in admixture with a co-catalyst selected from the elements of Groups V-B, VI-B and the Actinide series of the Periodic Table.

Among other factors, the present invention is based on my discovery that alcohols can be converted to useful oxygenated products having at least one more carbon atom than the starting alcohol in improved yield and selectivity by utilizing a heterogeneous bimetallic sulfided catalyst system.

An advantage of the present process lies in the fact that the heterogeneous catalyst employed is easier to separate from the reaction products than the homogeneous catalysts of the prior art.

In addition, it has been found that the present process does not require any soluble promoters or co-catalysts. This is particularly advantageous, since the absence of a halide promoter in the system obviates the need for expensive corrosion resistant equipment.

Oxygen-containing carbon compounds obtained with high selectivity in the process of the invention are carboxylic acids, alcohols, aldehydes or the secondary products which may be formed therefrom under the reaction conditions in a subsequent reaction, for example, esterification, condensation or dehydration.

DETAILED DESCRIPTION OF THE INVENTION

Illustrative of a typical batch procedure, the alcohol is charged to a high pressure reactor, and then there is introduced a heterogeneous bimetallic sulfided catalyst system comprising nickel and an element of Groups V-B, VI-B or the Actinide series. The reactor is pressurized with a mixture containing carbon monoxide and hydrogen and heated for a suitable length of time to give the desired conversion. Liquid and gaseous products and reactants can be easily separated from the catalyst by filtration, distillation or other methods. Unreacted starting materials can be recycled. The products can be isolated by a number of known methods, including distillation. In some cases it may be advantageous to further process the products. For example, methyl acetate can be easily hydrolyzed to acetic acid.

The process of the present invention can also be run in a continuous fashion. This is particularly advantageous as the catalyst is not soluble in the reaction medium. A number of reactor configurations are suitable including fixed and fluid beds, slurry beds and stirred tank reactors. As with a batch reaction, unreacted starting materials can be easily recycled and, if desired, the products can be further processed.

The alcohols suitable for use in the present invention may be primary, secondary, tertiary or benzylic alcohols having from one to about twenty carbon atoms. Diols and polyols may also be used. A preferred alcohol is methanol. If desired, the reactant alcohol may be diluted with an alcohol-miscible solvent such as dioxane, tetrahydrofuran, N-methylpyrolidinone, and the like. When methanol is used as the starting alcohol, reaction products typically formed include acetic acid, ethanol, acetaldehyde or methyl acetate.

The heterogeneous bimetallic sulfided catalyst system employed in the present process comprises a composite of sulfides of a nickel component and a Group V-B, VI-B or Actinide component. Co-catalysts suitable for admixture with the nickel component include tantalum, chromium, vanadium, thorium and tungsten. A particularly preferred catalyst system comprises nickel and molybdenum. The catalyst system may optionally contain phosphorus or silicon.

In carrying out the reaction, it is usually desirable, although not essential, to place the catalyst on a support. Various supports suitable for use in the process are described in the prior art. Generally, the support should be a solid, inert material which is relatively insoluble in the solvent employed. Suitable supports include various treated or untreated organic and inorganic supports. Included among these are synthetic and naturally occurring polymers, alumina, silica, titania, silica-alumina, zeolites, glass, carbon, and the like. Particularly preferred supports are alumina and silica-alumina.

The metals may be added to the support using a number of methods known to the art such as by impregnation, co-precipitation, and the like. The method of loading the catalyst on the support will depend on the nature and composition of the support. Generally, the most convenient method of depositing the metals on the support is by adding a solution of metal salts to the support and subsequently converting them to an insoluble form.

An especially suitable catalyst precursor may be prepared by impregnating alumina with an aqueous or organic solution of the metal salts, either together or sequentially, followed by drying and calcining to give the metal oxides.

The catalyst may be converted to its active sulfide form by any of a number of conventional procedures. Treatment with hydrogen sulfide or other sulfur-containing compounds such as carbon disulfide, dimethyl disulfide or sulfur, in the presence of hydrogen or synthesis gas is effective. This treatment can be either prior to or concurrent with the alcohol carbonylation reaction.

In the process of the present invention alcohols are reacted with carbon monoxide and hydrogen (synthesis gas). Synthesis gas produced by the reaction of carbonaceous material with water is suitable. Mixtures of carbon dioxide and hydrogen, carbon monoxide and water, and the like, may also be employed. Whether introduced originally, or produced in situ under processing conditions, the reaction elements of carbon monoxide and hydrogen are required.

The relative molar quantities of carbon monoxide and hydrogen present during the reaction can vary in the range between about 10:1 and 1:10, and preferably in the range between about 3:1 and 1:3. An inert diluent gas such as nitrogen or helium may be included if desired.

The carbonylation reaction requires a relatively high pressure for optimum selectivity and yield of product. The pressure is maintained in the range between about 500 psig and 5,000 psig, and preferably in the range between about 800 psig and 2000 psig.

The reaction is conducted at a temperature in the range between about 150° C. and 350° C., and preferably in the range between about 190° C. and 290° C.

The time that the reactants are in contact with the catalyst will be dependent, among other factors, on the temperature, pressure, alcohol reactant, catalyst, reactor configuration and the desired level of conversion.

The solid catalyst can be easily separated from the generally liquid and gaseous reaction products and unreacted starting materials by, for example, filtration, centrifugation, settling out or distillation. The catalyst can be reused in a subsequent reaction. Unreacted starting materials can be separated from reaction products and are suitable for recycle in the process.

The products of the reaction, which can be isolated by a number of well-known methods such as distillation, are generally useful as solvents or chemical intermediates. In some cases it may be advantageous to further process the reaction products by well-known means to other useful products. For example, methyl acetate can be hydrolyzed to acetic acid, and ethanol and phenethyl alcohol can be dehydrated to ethylene and styrene, respectively.

The following examples are provided to illustrate the invention in accordance with the principles of this invention but are not to be construed as limiting the invention in any way except as indicated by the appended claims.

EXAMPLES

EXAMPLE 1

A catalyst was prepared from nickel nitrate hexahydrate (8.1 g) and commercial phosphomolybdic acid (15.1 g) by dissolving in water (50 ml), evaporating to dryness on a hot plate, and further heating first at 200° C. for 2 hours and finally at 325° C. for 2 hours to yield 13.4 g of a dark brown solid. This catalyst was used in Example 4.

EXAMPLE 2

A catalyst was prepared by impregnating 50 g of alumina with a water solution (32 ml) of nickel nitrate hexahydrate (8.6 g) and silicotungstic acid hydrate (10.3 g). The catalyst was dried under vacuum at 120° C. and then calcined in air at 475° C. for 4 hours. This catalyst was used in Example 8-g.

EXAMPLE 3

A catalyst was prepared by impregnating 50 g of a commercial vanadium oxide on alumina catalyst (Girdler V-0301) with a water solution (32 ml) of nickel nitrate hexahydrate (7.8 g). The catalyst was dried at 120° C. and then calcined at 475° C. for 4 hours. This catalyst was used in Example 8-e.

EXAMPLE 4

A 300 ml stainless steel autoclave was charged with 75 ml of methanol and 5.0 g of an unsupported catalyst comprising nickel, molybdenum and phosphorus oxides (as described in Example 1) that had been treated with 10% hydrogen sulfide in hydrogen at 325° C. followed by hydrogen at 400° C. The reactor was sealed and pressurized to 1000 psi with a mixture of one part hydrogen and two parts carbon monoxide, then heated to 235° C. After 6.0 hours the reactor was cooled and the pressure released. Analysis of the liquid products by gas chromatography indicated methyl acetate (121 mmol) and ethanol (12.8 mmol) as major products as well as minor amounts of n-propanol and acetic acid.

EXAMPLE 5

A 300 ml stainless steel autoclave was charged with 10.00 g of a catalyst comprising nickel, molybdenum and phosphorus (approximately 3, 14 and less than 1 wt. %, respectively) oxides on alumina, 2.50 g of sulfur and 50 ml of methanol. The reactor was sealed, flushed with nitrogen, and pressurized to 900 psi with a mixture of two parts hydrogen and one part carbon monoxide. The reactor was heated to 250° C. and the pressure adjusted to 2500 psi. After 4 hours, the reactor was cooled with ice and the pressure released. Analysis of the liquid product by gas chromatography, after addition of 1,4-dioxane as internal standard, indicated methyl acetate (27.3 mmol) and ethanol (12.4 mmol) as products as well as methyl ether and methyl sulfide.

EXAMPLE 6

A 300 ml stainless steel autoclave was purged with nitrogen and charged with 100 ml of methanol, 1,4-dioxane (as internal standard), and 5.0 g of a catalyst comprising nickel, molybdenum and phosphorus (approximately 6, 15 and 2 wt. %, respectively) oxides on silica-alumina that had been previously treated with 10% hydrogen sulfide in hydrogen at 325° C. The autoclave was sealed and pressurized with 350 psi of a mixture of two parts hydrogen and one part carbon monoxide, then heated to 240° C. to give a final pressure of 1200 psi. After 2 hours, analysis of a small sample indicated methyl acetate (7.8 mmol) and ethanol (0.25 mmol) as major products.

This example was repeated except that the initial pressure was 1000 psi and the final pressure was 2300 psi. In this case, the products after two hours of reaction were methyl acetate (34.0 mmol) and ethanol (7.8 mmol).

EXAMPLE 7

Four 18 ml stainless steel reactors were each charged with 5 ml of methanol and 0.50 g of a catalyst comprising nickel, molybdenum and phosphorus (approximately 3, 13 and 2 wt. %, respectively) oxides on alumina. Reactors 1–3 each contained a source of sulfur as indicated in Table 1. The reactors were sealed and pressurized to 850 psi with a mixture of 2 parts hydrogen and 1 part carbon monoxide. The reactors were heated at 240° C. with gentle shaking for 4.0 hours. After cooling and venting, the contents of the reactors were analyzed by gas chromatography. The results are indicated in Table 1. In addition to the indicated products, methyl ether and methyl sulfide were also produced.

TABLE 1

| Charges | | Products | |
|---|---|---|---|
| Sulfur Compound | Amount | Methyl Acetate | Ethanol |
| 1. Methyl disulfide | 0.7 mmol | 0.2 mmol | trace |
| 2. Carbon disulfide | 1.2 | 1.2 | 0.3 mmol |
| 3. Sulfur | 1.6 | 0.4 | 0.1 |
| 4. None | 0 | trace | 0 |

EXAMPLE 8

A series of 18 ml stainless steel reactors were each charged with methanol (5 ml), 1,4-dioxane (0.10 ml), sulfur (0.13 g) and catalyst (0.50 g) as indicated in Table 2. The reactors were sealed and pressurized with 900 psi of a mixture of two parts hydrogen and one part carbon monoxide. The reactors were heated at 240° C. with gentle shaking for 4.0 hous. After cooling and venting, the contents were analyzed by gas chromatography using 1,4-dioxane as internal standard. In addition to the products indicated, methyl ether and methyl sulfide were also formed.

TABLE 2

| Catalyst[1] | Products | |
|---|---|---|
| | Methyl Acetate | Ethanol |
| a. Ni(8), W(19), Ti(8) on silica-alumina | 3.6 mmol | 0.3 mmol |
| b. Ni(3), Mo(12), P(0.3) on silica | 2.1 | 0.3 |
| c. Ni(3), Mo(12) on alumina | 0.4 | 0.2 |
| d. Ni(3), Ta(12) on alumina | 1.7 | 0.1 |
| e. Ni(3), V(10) on alumina | 0.6 | 0.03 |
| f. Ni(3), Th(12) on alumina | 0.2 | 0 |
| g. Ni(3), W(12), Si(0.2) on alumina | 1.0 | 0.1 |
| h. Ni(6), Mo(15), P(2) on silica-alumina | 4.4 | 0.9 |

[1]Approximate weight percent of metal in parenthesis, present in oxide form.

EXAMPLE 9

An 18 ml stainless steel reactor was charged with 5 ml ethanol, 0.125 g sulfur, and 0.50 g of a catalyst comprising nickel, molybdenum, and phosphorus (approximately 6, 15, and 2 wt. %) oxides on silica-alumina. The reactor was sealed and pressurized to 900 psi with a mixture of 2 parts hydrogen and 1 part carbon monoxide, then heated with gentle shaking for 4.0 hours at 240° C. After cooling and releasing the pressure, analysis indicated ethyl propionate (1.2 mmol) and n-propanol (0.6 mmol) as the major carbonylation products along with an undetermined amount of ethyl ether.

EXAMPLE 10

An 18 ml stainless steel reactor was charged with 5 ml of 1,3-propanediol, 0.125 g of sulfur, and 0.50 g of a catalyst comprising nickel, molybdenum, and phosphorous (approximately 6, 15, and 2 wt. %) oxides on silica-alumina. The reactor was sealed, pressurized with 900 psi of a mixture of two parts hydrogen and one part carbon monoxide, then heated with gentle shaking to 240° C. for 4.0 hours. After cooling and releasing the pressure, gas chromatographic analysis indicated the presence of gamma-butyrolactone.

Example 11

Two 18 ml stainless steel reactors were each charged with 1 ml of methanol, 0.125 g sulfur, 0.50 g of a catalyst comprising nickel, molybdenum, and phosphorus (approximately 6, 15, and 2 wt. %) oxides on silica-alumina. Additionally one reactor was charged with 4 ml N-methylpyrolidinone and the other with 4 ml of tetrahydrofuran. The reactors were sealed and pressurized to 900 psi with a mixture of 2 parts hydrogen and 1 part carbon monoxide. The reactors were heated with gentle shaking for 4.0 hours at 240° C. Analysis of the products indicated 0.6 mmol methyl acetate and minor amounts of acetaldehyde and ethanol in the first, and 1.86 mmol of methyl acetate in the second as well as methyl ether and methyl sulfide in both.

EXAMPLE 12

A stainless steel reactor tube was packed with 5.0 g of catalyst comprising nickel, molybdenum, and phosphorous (approximately 3, 13, and 2 wt. %) oxides on alumina. The catalyst was treated with 10% hydrogen sulfide in hydrogen at 325° C. for 1 hour, then purged with nitrogen. The catalyst bed was maintained at 280° C. as synthesis gas (comprising two parts hydrogen and one part carbon monoxide) and methanol were passed over the catalyst. The reactor pressure was maintained between 1720 and 1760 psi, the GHSV at 4000 hr.$^{-1}$ and LHSV at 2 hr.$^{-1}$. Analysis of the products collected over a 20.5-hour period indicated methyl acetate (79.2 mmol) and ethanol (102.2 mmol) as major carbonylation products as well as lesser amounts of acetic acid. Methyl ether was also formed.

What is claimed is:

1. A process for the preparation of a mixture of oxygenated products selected from carboxylic acids, alcohols, aldehydes and carboxylic acid esters which comprises reacting a primary, secondary, or tertiary alcohol having from one to about twenty carbon atoms with hydrogen and carbon monoxide at a temperature in the range of about 150° C. to 350° C. and a pressure in the range of about 500 psig to 5,000 psig in the presence of a heterogeneous sulfided catalyst comprising a composite of sulfides of a nickel component and a Group V-B, VI-B or Actinide element component cocatalyst and in the absence of a halide promoter wherein the reaction products formed have at least one more carbon atom than the starting alcohol.

2. The process according to claim 1, wherein the sulfided catalyst contains nickel and molybdenum.

3. The process according to claim 1, wherein the sulfided catalyst further comprises phosphorus or silicon.

4. The process according to claim 1, wherein the sulfided catalyst is present on a support.

5. The process according to claim 4, wherein the support is alumina or silica-alumina.

6. A process for the preparation of a mixture of oxygenated products selected from acetic acid, ethanol, acetaldehyde, methyl acetate and methyl ether which comprises reacting methanol with hydrogen and carbon monoxide at a temperature in the range of about 150° C. to 350° C. and a pressure in the range of about 500 psig to 5,000 psig in the presence of a heterogeneous sulfided catalyst comprising a composite of sulfides of a nickel component and a Group V-B, VI-B or Actinide element component cocatalyst and in the absence of a halide promoter.

7. The process according to claim 6, wherein the sulfided catalyst contains nickel and molybdenum.

8. The process according to claim 6, wherein the sulfided catalyst further comprises phosphorus or silicon.

9. The process according to claim 6, wherein the sulfided catalyst is present on a support.

10. The process according to claim 9, wherein the support is alumina or silica-alumina.

* * * * *